United States Patent [19]

Varani et al.

[11] Patent Number: 4,829,004
[45] Date of Patent: May 9, 1989

[54] ROLLER BOTTLE SYSTEM

[75] Inventors: James Varani; David E. Solomon; William J. Hillegas; David L. Melmoth, all of Ann Arbor, Mich.

[73] Assignees: The University of Michigan; Solohill Engineering Inc., both of Ann Arbor, Mich.

[21] Appl. No.: 124,699

[22] Filed: Nov. 24, 1987

[51] Int. Cl.$^4$ .............................................. C12M 1/24
[52] U.S. Cl. ................................... 435/296; 435/285; 366/233
[58] Field of Search ............... 435/284, 285, 286, 296, 435/306, 307; 366/233, 234; 428/131

[56] References Cited

U.S. PATENT DOCUMENTS

| | | | |
|---|---|---|---|
| 707,986 | 8/1902 | Tolhurst et al. | 366/234 |
| 3,941,661 | 3/1976 | Noteboom | 435/285 |
| 4,062,995 | 12/1977 | Korpman | 428/131 |
| 4,167,599 | 9/1979 | Nissinen | 428/131 |
| 4,317,886 | 3/1982 | Johnson et al. | 435/285 |
| 4,535,020 | 8/1985 | Thomas et al. | 428/131 |
| 4,600,622 | 7/1986 | Carlson et al. | 428/131 |
| 4,734,373 | 3/1988 | Bartal | 435/296 |

Primary Examiner—Samuel Scott
Assistant Examiner—Noah Kamen
Attorney, Agent, or Firm—Rohm & Monsanto

[57] ABSTRACT

An insert for a roller bottle of the type used in cell culture for vaccine manufacture is formed of a polymeric resilient material whereby it can be bent or rolled so that it can pass through the opening of the roller bottle. Once the insert is inside the bottle, it is released so that its resilient characteristic causes it to unbend or unroll. The insert is wider than the diameter of the roller bottle, and therefore it is urged against the interior wall of the roller bottle. Apertures and/or notches are provided in the insert to increase the turbulence of a fluid and to decrease the fluidic shear forces in the roller bottle as it is rotated in conventional operation. A significant increase in productivity is achieved because particles, which may be microcarrier beads, are maintained in suspension, and prevented from sinking to the bottom of the fluid medium where cells cannot grow. The roller bottle system is thereby transformed into a microcarrier suspension culture system.

14 Claims, 2 Drawing Sheets

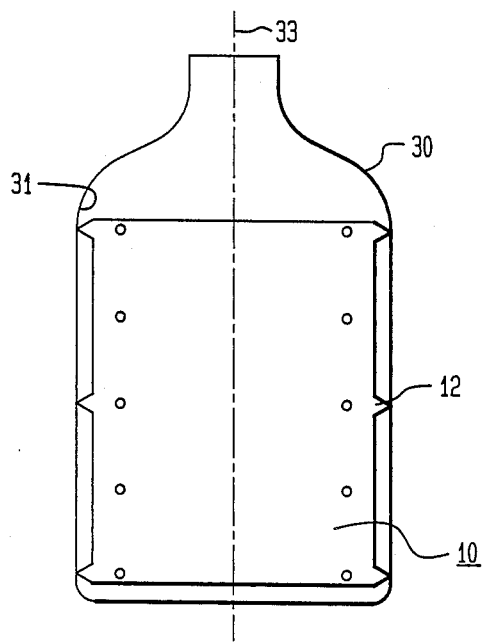

ROLLER BOTTLE SYSTEM

BACKGROUND OF THE INVENTION

This invention relates generally to cell culture systems, and more particularly, to a stirring device which is particularly adapted for use in combination with roller bottles.

Roller bottle cell culturing systems are in widespread use in the manufacture of cell culture vaccines. In a typical roller bottle system, a plurality of cylindrical bottles contain a cell growth medium, preferably a liquid, which is rotated during cell growth. However, the productivity of this known arrangement is low, and efforts have been made in the prior art to improve the performance.

One effort at increasing the productivity of roller bottle arrangements involves the use of microcarrier beads in the fluid culture media. At the low speeds at which the roller bottles are rotated, the microcarrier beads sink to the bottom of the fluid culture media, and very little additional growth occurs. Additionally, since the fluid culture media collects at the bottom of the rotating roller bottle during operation, only a small amount of media can be used in the roller bottle.

Prior art efforts at stirring or agitating the cell culture medium have produced systems which are complex and expensive. Moreover, such systems cannot be retrofitted to roller bottle systems which are in widespread use. Thus, those manufacturers which have invested in roller bottle systems would be required to suffer economic loss if they were to convert their production facilities. There is clearly a need for a an improvement to roller bottle systems which is not only simple and inexpensive, but can be employed in existing roller bottle arrangements.

It is, therefore, an object of this invention to provide a simple and economical system for increasing the productivity of roller bottle systems.

It is another object of this invention to provide an arrangement for maintaining particulate matter in suspension in roller bottle systems.

It is also an object of this invention to provide a roller bottle arrangement which can be used with microcarrier beads.

It is a further object of this invention to provide a roller bottle system which operates with increased productivity and which permits use of greater amounts of fluid medium.

It is additionally an object of this invention to provide a system for improving the productivity of roller bottle systems in a manner which can be implemented in existing roller bottle equipment.

It is yet a further object of this invention to provide an arrangement for maintaining particulate matter, such as microcarrier beads, in suspension in roller bottle systems which are rotated at slow speeds.

It is also another object of this invention to provide an improvement to roller bottle systems which is sufficiently economical and inexpensive as to be disposable after a limited number of uses.

It is yet an additional object of this invention to provide a stirring device for a microcarrier bead production system.

It is still another object of this invention to provide a system which permits a roller bottle arrangement to operate using a greater quantity of culture media, in combination with microcarrier beads.

SUMMARY OF THE INVENTION

The foregoing and other objects are achieved by this invention which provides an insert for maintaining particulate matter in suspension in a fluid during operation of a roller bottle system. The roller bottle itself may be of a known type having an interior surface defining an interior volume. Such an interior volume is characterized by a predetermined internal longitudinal length and a predetermined internal diameter. Moreover, the roller bottle is provided with a closable opening through which is gained access to the interior volume of the roller bottle. In accordance with one aspect of the invention, the insert is formed of a sheet of resilient material and has a longitudinal length which is shorter than the predetermined internal longitudinal length and a maximum width which is not less than the predetermined internal diameter. While the insert is in an undeployed state, it is inserted into the roller bottle through the closable opening. After insertion into the roller bottle, the insert is released, illustratively by operation of its own resilience, and assumes a deployed state where its edges are urged against the interior surface of the roller bottle.

In accordance with the invention, the resilient material which forms the insert is a polymeric material, such as polystyrene or polypropylene, while the roller bottle itself may be formed either of a polymeric material or glass. In this undeployed state, the resilient material of the insert is bent so that the sheet can be passed through the opening of the roller bottle. Such bending may include folding, or rolling. Once inside the roller bottle, however, the insert is released whereby it unbends by operation of its own resilience, and endeavors to straighten itself to the extent permitted by the interior wall of the roller bottle, which preferably is cylindrical in shape. In such an embodiment where the roller bottle has a substantially cylindrical interior, the deployed insert is disposed substantially in a diameter plane of the roller bottle.

In certain embodiments of the invention, the sheet of resilient material has a plurality of apertures therethrough for increasing turbulence in the fluid and maintaining the particulate matter in suspension as the roller bottle is rotated. Additionally, the sheet of resilient material may also be provided with a plurality of notches therethrough for increasing turbulence in the fluid and maintaining the particulate matter in suspension as the roller bottle is rotated. In other embodiments, a plurality of inserts can be installed in a roller bottle. Such inserts can be engaged with one another, such as by means of respective, mutually cooperating slits therein.

In accordance with a further aspect of the invention, an arrangement is provided for maintaining a particulate matter in suspension in a fluid, the arrangement is formed of the combination of a bottle having an interior surface defining an interior volume characterized by a predetermined internal longitudinal length and a predetermined internal diameter. As previously noted, the bottle is provided with a closable opening for facilitating access to the interior volume thereof. In most cases, the closable opening is smaller than the predetermined internal diameter of the bottle, and the insert is installed therethrough while it is in the undeployed state during which the insert is bent or coiled and inserted into the bottle.

In one embodiment, the insert is provided along its longitudinal edge with engagement members. The engagement members communicate with the interior surface of the bottle, and may be arranged in predetermined relation to one another for permitting the fluid to flow therebetween while the bottle is rotated in a conventional manner.

In a particularly advantageous embodiment of the invention, the fluid is a medium for cell growth (fluid culture media), and there are further provided a multiplicity of microcarrier beads therein. The insert operates, during rotation of the bottle, as a paddle to maintain the microcarrier beads in suspension, and prevent them from sinking to the bottom of the medium where cells cannot grow. The use of microcarrier beads in this invention results in a significant increase in productivity, while also achieving efficient utilization of the fluid culture media.

BRIEF DESCRIPTION OF THE DRAWING

Comprehension of the invention is facilitated by reading the following detailed description, in conjunction with the annexed drawing, in which:

FIG. 3 is a plan view of the insert of FIG. 1 installed in a bottle.

DETAILED DESCRIPTION

Figure 1:
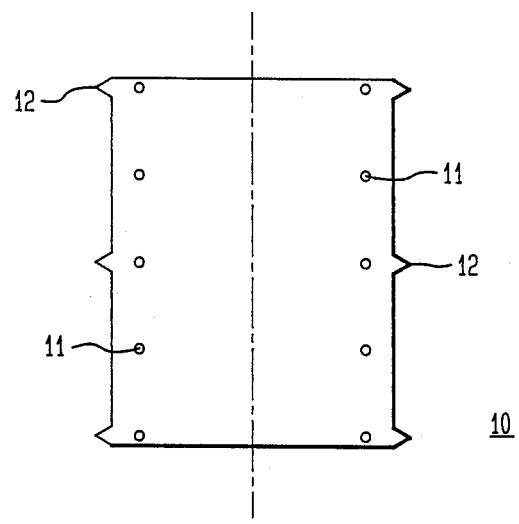
FIG. 1 is a plan view of a specific illustrative embodiment of an insert for a roller bottle, the insert being structured in accordance with the invention.

FIG. 1 is a plan view of a specific illustrative embodiment of an insert 10 for a roller bottle which is not shown in this figure. As shown, insert 10 is provided with a plurality of apertures 11 therethrough. Such apertures have the effect of causing the fluid medium (not shown) to undergo turbulence during rotation of the roller bottle. The turbulence in the fluid operates to maintain particulate matter in the fluid in suspension. In embodiments of the invention where microcarrier beads are disposed in the fluid, the turbulence ensures that the microcarrier beads remain in suspension, and that they do not sink. Sinking would cause an accumulation of microcarrier beads at the bottom of the fluid, inhibiting cell growth.

In this embodiment, insert 10 is provided with edge portions 12. As will be described herein, edge portions 12 are intended to be urged into communication with the interior surface of the roller bottle, but some flow of the fluid is permitted between the interior wall of the roller bottle and the insert, between edge portions 12.

Figure 2:
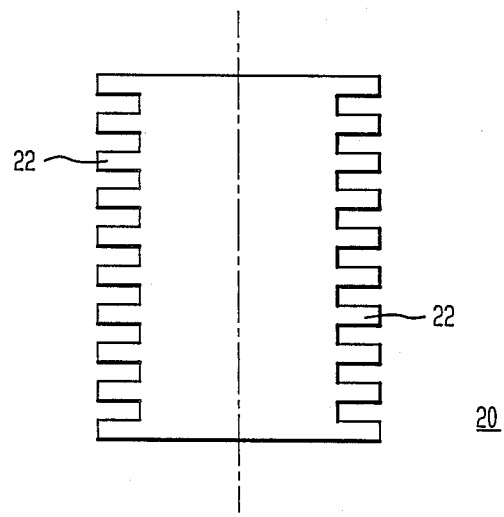
FIG. 2 is a plan view of a further specific illustrative embodiment of an insert for a roller bottle, the insert being structured in accordance with the invention.

FIG. 2 is a plan view of an insert 20, which is a further specific illustrative embodiment of a roller bottle, in accordance with the invention. In this embodiment, insert 20 is provided with a multiplicity of edge portions 22 which, in a manner similar to that indicated hereinabove, are also intended to be urged into communication with the interior surface of the roller bottle. Although this embodiment is not provided with apertures, as described hereinabove with respect to FIG. 1, fluid flow is permitted along the interior wall of the roller bottle, between the edge portions.

FIG. 3 is a plan view of insert 10 of FIG. 1 installed in a bottle 30. As shown, edge portions 12 of insert 10 are in contact with interior wall 31 of bottle 30. Thus, when this bottle is rotated about axis 33, in a conventional manner, insert 10 causes a turbulence in a fluid (not shown) which causes microcarrier beads (not shown) to remain in suspension. The use of microcarrier beads in combination with a roller bottle, such as bottle 30, significantly increases the productivity of the overall system.

The use of an insert of the type described herein in a roller bottle permits the roller bottle to be approximately one-third filled with culture media, as compared with the conventional practice of placing only a small amount of the media in a roller bottle. The use of microcarrier beads in a roller bottle system, as described herein, will increase virus yields by some 5–10 times normal yields of conventional roller bottle arrangements.

Although the invention has been described in terms of specific embodiments and applications, persons skilled in the art can, in light of this teaching, generate additional embodiments without exceeding the scope or departing from the spirit of the claimed invention. For example, the claimed invention encompasses within its scope inserts which are themselves adapted to be used in combination with other inserts, as well as cell culture systems wherein plural inserts are contained within a roller bottle. Accordingly, it is to be understood that the drawing and description in this disclosure are proffered to facilitate comprehension of the invention, and should not be construed to limit the scope thereof.

What is claimed is:

1. A roller bottle system comprising:
   roller bottle means having an interior surface defining an interior volume characterized by a predetermined internal longitudinal length, a predeterminable internal width measured transverse to said predetermined internal longitudinal length, and a predetermined internal perimeter measured transverse to said predetermined internal longitudinal length, said roller bottle means further having a closable opening through which access to said interior volume of said roller bottle means is obtained; and
   insert sheet means for maintaining particulate matter in suspension in a fluid during operation of said roller bottle means, said insert sheet means being formed of resilient material having a longitudinal length which is shorter than said predetermined internal longitudinal length and a width dimension which is greater than said predetermined internal width and shorter than said predetermined internal perimeter, said insert sheet means having an undeployed state during which said insert sheet means is inserted into said roller bottle means through said closable opening, and a deployed state after said insert sheet means is inserted into said roller bottle means, said insert sheet means further having:
   first and second longitudinal edge portions arranged along respective first and second longitudinal edges thereof, said first and second longitudinal edges being distal from one another by a distance corresponding to said width dimension, said first and second longitudinal edge portions being urged against respective portions of said interior surface of said roller bottle means during said deployed state.

2. The roller bottle system of claim 1 wherein said insert sheet means is formed of a resilient polymeric material.

3. The roller bottle system of claim 2 wherein said insert sheet means is formed of polystyrene.

4. The roller bottle system of claim 2 wherein said insert sheet means is formed of polypropylene.

5. The roller bottle system of claim 2 wherein said insert sheet means has a plurality of apertures therethrough for increasing turbulence in the fluid and maintaining the particulate matter in suspension as said roller bottle means is operated.

6. The roller bottle system of claim 1 wherein said sheet of resilient material has a plurality of notches therethrough for increasing turbulence in the fluid and maintaining the particulate matter in suspension as said roller bottle means is operated.

7. The roller bottle system of claim 1 wherein said first and second edge portions are each provided with an engagement portion for communicating with said interior surface of said roller bottle means, and a cut-out region for permitting fluid flow in the vicinity of said interior surface during operation of said roller bottle means.

8. An arrangement for maintaining a particulate matter in suspension in a fluid, the arrangement comprising:
   bottle means having a substantially cylindrical interior surface defining an interior volume characterized by a predetermined internal longitudinal length and a predetermined internal diameter, said bottle means having a closable opening for facilitating access to the interior volume of the roller bottle, said closable opening being smaller than said predetermined internal diameter; and
   insert means formed of a sheet of a resilient material having a longitudinal length which is shorter than said predetermined internal longitudinal length and a maximum width which is at least equal to said predetermined internal diameter of said bottle means, and less than a circumference dimension of said bottle means, said insert means being formed of a bendable resilient material, having an undeployed state during which said insert means is bent and inserted into said bottle means through said closable opening, and a deployed state after said insert means is inserted into said bottle means, at least an engagement portion on each side of said insert means, during said deployed state, being urged against said interior surface of said bottle means.

9. The arrangement of claim 8 wherein there is further provided engagement members in said engagement portion of said insert means, said engagement members communicating with said interior surface of said bottle means.

10. The arrangement of claim 9 wherein said engagement members are arranged in spaced apart relation to one another for permitting the fluid to flow between said interior surface of said bottle means and said insert means.

11. The arrangement of claim 8 wherein said insert means is formed of polystyrene.

12. The arrangement of claim 8 wherein said insert means is formed of polypropylene.

13. The arrangement of claim 8 wherein there is provided a plurality of apertures in said insert means for increasing turbulence in the fluid during operation of the arrangement.

14. The arrangement of claim 8 wherein there is further provided microcarrier means suspended in the fluid in response to said insert means.

* * * * *